(12) United States Patent
Toyoda et al.

(10) Patent No.: US 11,217,360 B2
(45) Date of Patent: Jan. 4, 2022

(54) ELECTRICALLY CONDUCTIVE COMPOSITION AND BIOSENSOR

(71) Applicant: NITTO DENKO CORPORATION, Ibaraki (JP)

(72) Inventors: Eiji Toyoda, Ibaraki (JP); Naoya Sugimoto, Ibaraki (JP); Ryoma Yoshioka, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 0 days.

(21) Appl. No.: 16/646,261

(22) PCT Filed: Jun. 25, 2018

(86) PCT No.: PCT/JP2018/023963
§ 371 (c)(1),
(2) Date: Mar. 11, 2020

(87) PCT Pub. No.: WO2019/049470
PCT Pub. Date: Mar. 14, 2019

(65) Prior Publication Data
US 2020/0286641 A1    Sep. 10, 2020

(30) Foreign Application Priority Data

Sep. 11, 2017   (JP) .............................. JP2017-174132

(51) Int. Cl.
*H01B 1/20*     (2006.01)
*C08K 5/053*    (2006.01)
(Continued)

(52) U.S. Cl.
CPC ................. *H01B 1/20* (2013.01); *A61B 5/25* (2021.01); *C08K 5/053* (2013.01); *C08L 101/14* (2013.01)

(58) Field of Classification Search
CPC ........ C08K 5/00; C08K 5/053; C08K 5/0025; C08L 101/12; C08L 101/14; C08L 29/04;
(Continued)

(56) References Cited

U.S. PATENT DOCUMENTS

2007/0257235 A1  11/2007  Park et al.
2011/0310053 A1  12/2011  Kim et al.
(Continued)

FOREIGN PATENT DOCUMENTS

CN    105764689 A    7/2016
CN    107109107 A    8/2017
(Continued)

OTHER PUBLICATIONS

International Search Report for corresponding international application PCT/JP2018/023963 dated Sep. 18, 2018, citing the above references.
(Continued)

*Primary Examiner* — Mark Kopec
*Assistant Examiner* — Jaison P Thomas
(74) *Attorney, Agent, or Firm* — Hauptman Ham, LLP

(57) ABSTRACT

The electrically conductive composition includes an electrical conductive polymer, a binder resin, and at least one of a cross-linking agent and a plasticizer.

5 Claims, 6 Drawing Sheets

(51) Int. Cl.
  *C08L 101/14* (2006.01)
  *A61B 5/25* (2021.01)
(58) Field of Classification Search
  CPC . C08L 65/00; H01L 31/20; A61B 5/25; A61B 5/0408; H01B 1/20; C08G 2261/11; C08G 2261/1424; C08G 2261/3223; C08G 2261/794; C08G 2261/94; C08G 61/126
  See application file for complete search history.

(56) References Cited

U.S. PATENT DOCUMENTS

| 2013/0284982 | A1* | 10/2013 | Chen | C09D 5/24 |
| | | | | 252/478 |
| 2014/0360763 | A1* | 12/2014 | Mizuguchi | C09D 7/40 |
| | | | | 174/257 |
| 2016/0177109 | A1* | 6/2016 | Hendricks | H01M 4/608 |
| | | | | 428/36.91 |
| 2017/0058167 | A1 | 3/2017 | Matsubayashi | |
| 2018/0192948 | A1 | 7/2018 | Okumura et al. | |
| 2018/0199443 | A1 | 7/2018 | Okumura et al. | |

FOREIGN PATENT DOCUMENTS

| EP | 0 612 498 A1 | 8/1994 |
| JP | 2011-238471 A | 11/2011 |
| JP | 2011-249104 A | 12/2011 |
| JP | 2013-75813 A | 4/2013 |
| JP | 2015-93167 A | 5/2015 |
| JP | 2017-22236 A | 1/2017 |
| JP | 2017-22237 A | 1/2017 |
| JP | 2017-43765 A | 3/2017 |
| WO | 2012/039240 A1 | 3/2012 |

OTHER PUBLICATIONS

Chang-hsiu Chen et al., "Mechanical characterizations of case Poly(3,4-ethylenedioxythiophene): Poly(styrenesulfonate)/Polyvinyl Alcohol thin films", Syntehtic Metals, 161 (2011), pp. 2259-2267.
Written Opinion for corresponding international application PCT/JP2018/023963 dated Sep. 18, 2018.
Extended European Search Report issued for corresponding European Patent Application No. 18852873.1 dated Jul. 19, 2021.
Cho et al., "Fabrication and characterization of conducting polyvinyl alcohol nanofibers", Materials Letters 68 (2012), pp. 293-295, cited in NPL No. 1.
Office Action issued for corresponding Japanese Patent Application No. 2017-174132 dated Jun. 15, 2021, along with an English machine translation.
Office Action issued for corresponding Chinese Patent Application No. 201880056937.7 dated Jul. 29, 2021, along with an English translation.
Office Action dated Oct. 7, 2021 for corresponding Taiwanese Patent Application No. 107123442, along with an English translation.

* cited by examiner

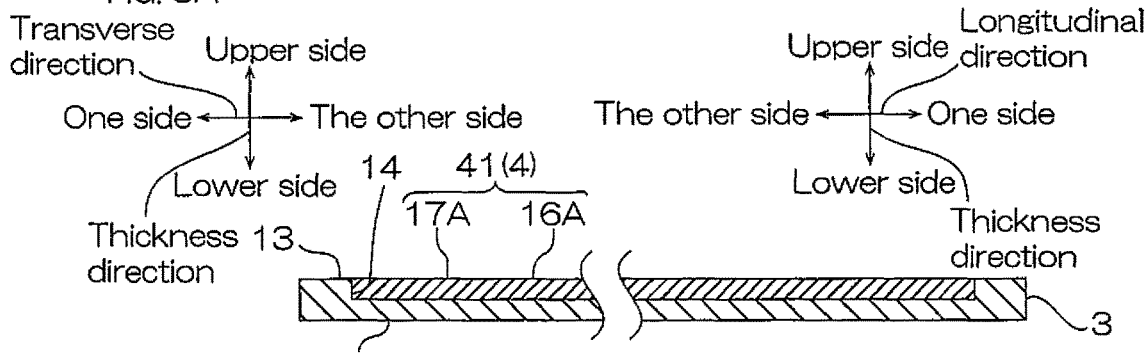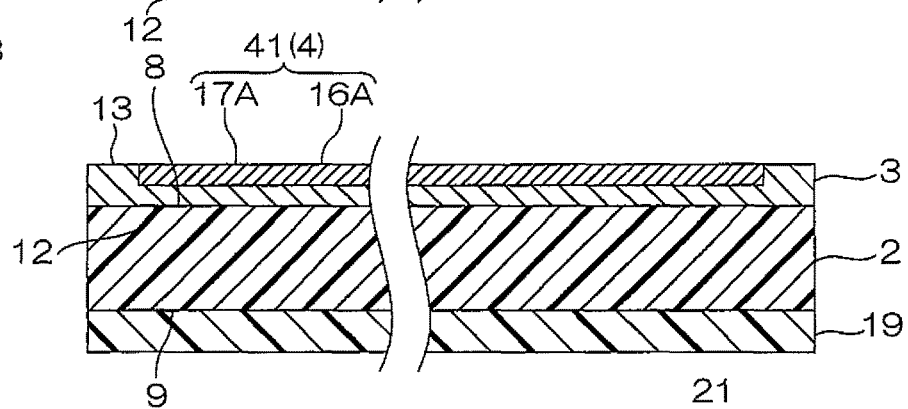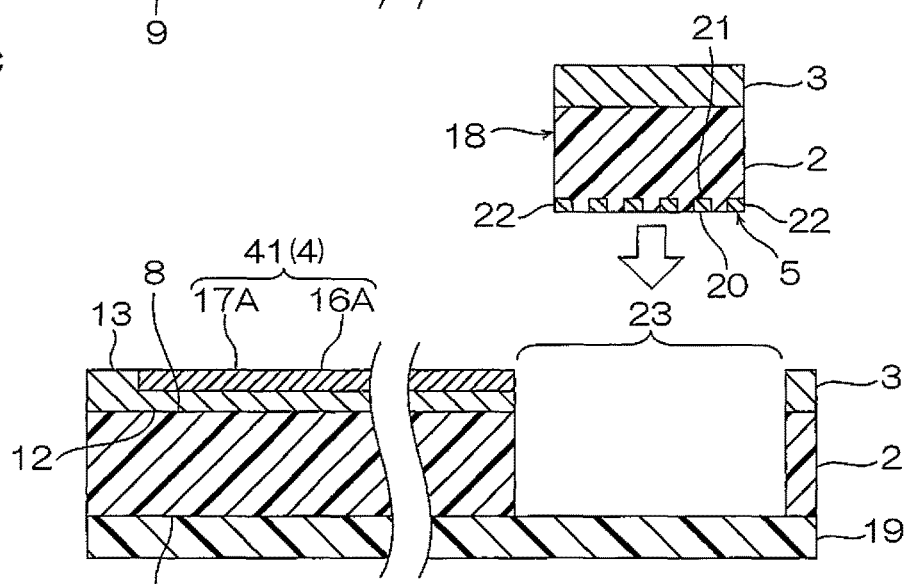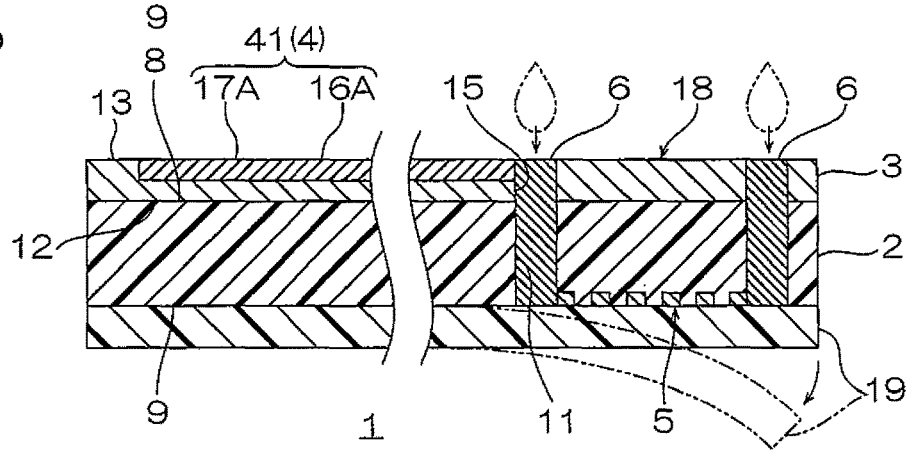

FIG. 5
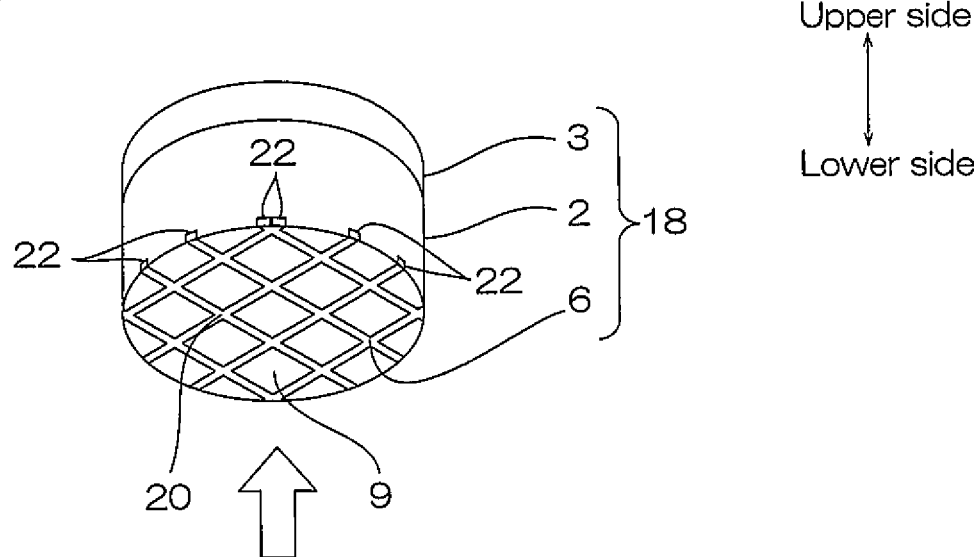
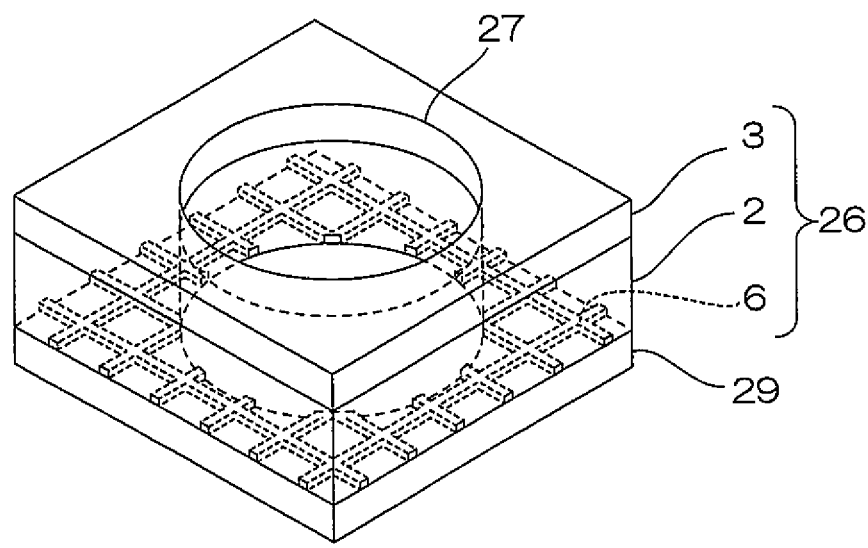

ELECTRICALLY CONDUCTIVE COMPOSITION AND BIOSENSOR

CROSS REFERENCE TO RELATED APPLICATION

This application claims the priority of Japanese Patent Application No. 2017-174132, filed on Sep. 11, 2017, in the JPO (Japanese Patent Office). Further, this application is the National Phase Application of International Application No. PCT/JP2018/023963, filed on Jun. 25, 2018, which designates the United States and was published in Japan. Both of the priority documents are hereby incorporated by reference in their entireties.

TECHNICAL FIELD

The present invention relates to an electrically conductive composition and a biosensor.

BACKGROUND ART

For the electrically conductive composition, a mixture of poly(3,4-ethylenedioxythiophene):poly(styrene sulfonate) (PEDOT-PSS) and polyvinyl alcohol (PVA) has been known (ref: for example, Non-Patent Document 1).

The mixture has excellent electrical conductivity and formability, and an electrically conductive object formed from this mixture (electrically conductive film) has excellent durability, tenacity, and flexibility.

CITATION LIST

Patent Document

Non-Patent Document 1: Synthetic Metals 161 (2011) 2259-2267

SUMMARY OF THE INVENTION

Problem to be Solved by the Invention

However, even more excellently high tenacity (To be specific, achieving both tensile strength and tensile elongation (elongation)) and flexibility may be required for the electrically conductive object.

The present invention provides an electrically conductive composition that allows for preparation of an electrically conductive object with high tenacity and flexibility, and a biosensor including a connector prepared from the electrically conductive composition.

Means for Solving the Problem

The present invention (1) includes an electrically conductive composition containing an electrical conductive polymer, binder resin, and at least one of a cross-linking agent and a plasticizer.

The present invention (2) includes the electrically conductive composition described in (1), containing both of the cross-linking agent and the plasticizer.

The present invention (3) includes the electrically conductive composition described in (1) or (2), wherein the binder resin is a water-soluble polymer.

The present invention (4) includes the electrically conductive composition described in any one of (1) to (3), wherein the cross-linking agent contains at least one selected from the group consisting of a zirconium compound, an isocyanate compound, and an aldehyde compound.

The present invention (5) includes the electrically conductive composition described in any one of (1) to (4), wherein the plasticizer contains a polyol compound.

The present invention (6) includes a biosensor including a wire layer, a probe that makes contact with a surface of a living body, and a connector that electrically connects the wire layer with the probe, wherein the connector includes the connector prepared from any one of the electrically conductive composition described in (1) to (5).

Effects of the Invention

The electrically conductive composition of the present invention contains any one of the cross-linking agent and plasticizer, and therefore an electrically conductive object with excellently high tenacity and flexibility can be prepared.

The biosensor of the present invention has excellent connection reliability.

BRIEF DESCRIPTION OF THE DRAWINGS

FIG. 2A is a cross sectional view along the line A-A, and FIG. 2B is a cross sectional view along the line B-B.

FIG. 3A to FIG. 3D are a process diagram of a production of the wearable biosensor shown in FIG. 2A, FIG. 3A illustrating a step of preparing a substrate layer and a wire layer, FIG. 3B illustrating a step of bonding a pressure-sensitive adhesive layer with the substrate layer, FIG. 3C illustrating a step of forming an opening and preparing a probe member, and FIG. 3D illustrating a step of inserting the probe member to the opening, and a step of forming a connector.

FIG. 5 shows perspective views illustrating production processes of a probe member, the upper side showing a perspective view seen from the lower side, and the lower side showing a perspective view seen from the upper side.

DESCRIPTION OF THE EMBODIMENTS

[Electrically Conductive Composition]

Figure 1:
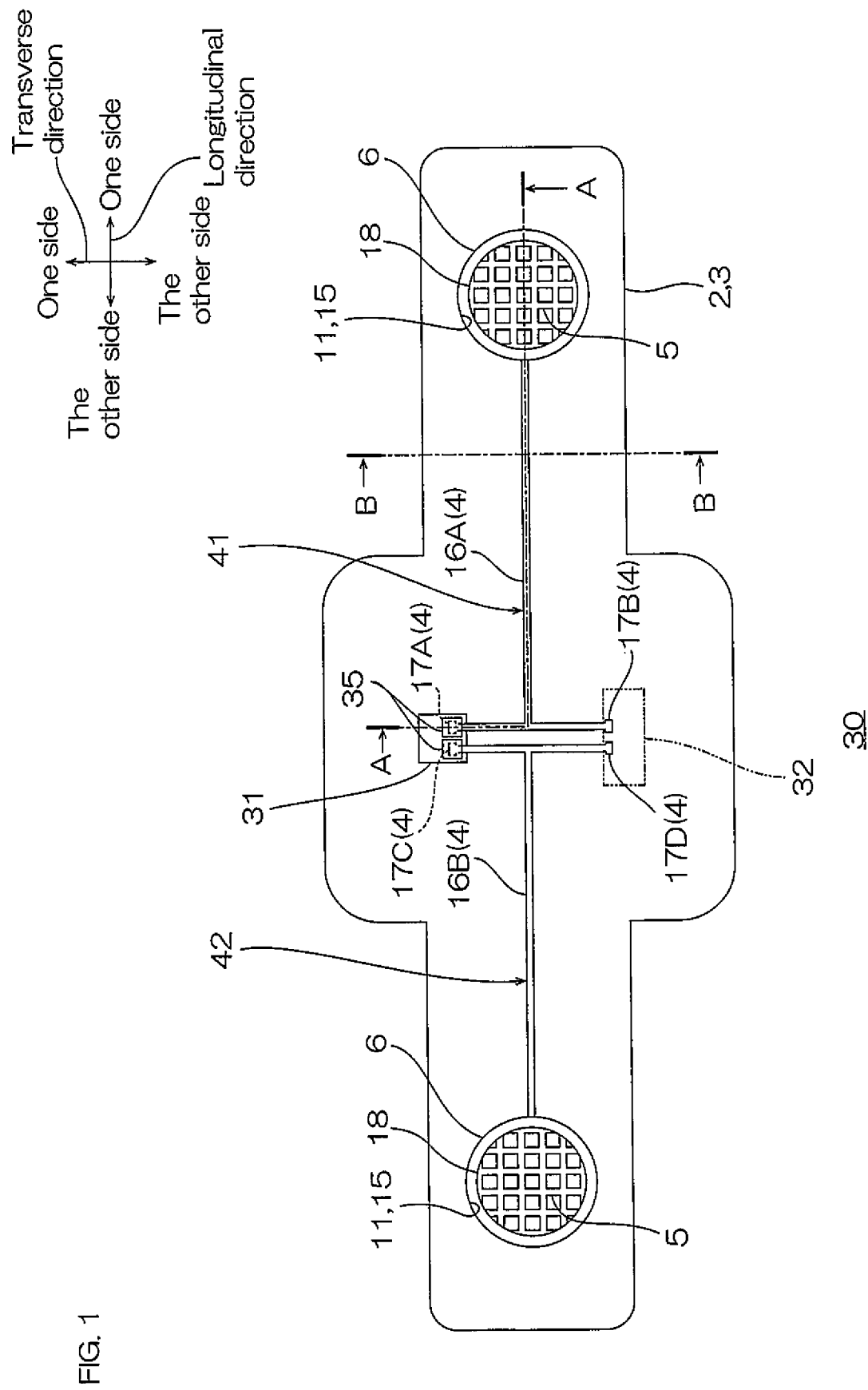
FIG. 1 shows a plan view of a wearable biosensor as an embodiment of the biosensor of the present invention.

The electrically conductive composition of the present invention contains an electrical conductive polymer, binder resin, and at least one of a cross-linking agent and a plasticizer.

[Components]

The electrical conductive polymer can give electrical conductivity to the electrically conductive composition (furthermore, electrically conductive object to be described later). Examples of the electrical conductive polymer include a polythiophene compound, polypyrrole compound, and polyaniline compound (To be specific, polyaniline, etc.). These can be used singly, or can be used in combination of two or more.

Preferably, the polythiophene compound, more preferably, (3,4-ethylenedioxy thiophene)/poly (4-styrene sulfonic acid)(hereinafter, may be referred to as PEDOT-PSS)) is used. With the PEDOT-PSS, excellent electrical conductivity can be given to the electrically conductive composition (furthermore, electrically conductive object to be described later).

The ratio of the electrical conductive polymer relative to the electrically conductive composition is, for example, 1 mass % or more, preferably 5 mass % or more, and for example, 40 mass % or less, preferably 20 mass % or less. When the ratio is the above-described lower limit or more, excellent electrical conductivity can be given to the electrically conductive composition (furthermore, electrically conductive object to be described later). When the ratio is the above-described upper limit or less, excellently high tenacity and flexibility can be given to the electrically conductive composition (furthermore, electrically conductive object to be described later).

The binder resin can give high tenacity to the electrically conductive composition (furthermore, electrically conductive object to be described later). Examples of the binder resin include a water-soluble polymer and water insoluble polymer. Preferably, in view of compatibility with other components in the electrically conductive composition, a water-soluble polymer is used. The water-soluble polymer does not completely dissolve in water, and includes polymers having hydrophilicity (hydrophilic polymer).

Examples of the water-soluble polymer include a hydroxyl group-containing polymer. For the hydroxyl group-containing polymer, for example, saccharides (agarose, etc.), for example, PVA, for example, polymer poly (acrylic acid-sodium acrylic acid) are used. Preferably, PVA is used. These can be used singly, or can be used in combination of two or more.

Examples of the PVA include polyvinyl alcohol, and for example, modified polyvinyl alcohol is used. Preferably, modified polyvinyl alcohol is used.

Examples of the modified polyvinyl alcohol include acetoacetyl group-containing poly vinyl alcohol, and diacetone acrylamide modified polyvinyl alcohol. Preferably, the acetoacetyl group-containing polyvinyl alcohol is used. The modified polyvinyl alcohol is described, for example, in Japanese Unexamined Patent Publication No. 2016-166436.

The ratio of the binder resin relative to the electrically conductive composition is, for example, 10 mass % or more, preferably 20 mass % or more, and for example, 50 mass % or less, preferably 35 mass % or less. When the ratio is the above-described lower limit or more, excellently high tenacity and flexibility can be given to the electrically conductive composition (furthermore, electrically conductive object to be described later). When the ratio is the above-described upper limit or less, excellent electrical conductivity can be given to the electrically conductive composition (furthermore, electrically conductive object to be described later).

The cross-linking agent and plasticizer are high tenacity/flexibility additives that can give high tenacity and flexibility to the electrically conductive composition (furthermore, electrically conductive object to be described later).

The high tenacity is characteristics that achieve both excellent strength and excellent elasticity. To be more specific, high tenacity means that strength and elasticity are both excellent in good balance, and does not include the case where one of the strength and elasticity is significantly excellent but the other is significantly low.

Flexibility is characteristics of suppressing generation of damages such as fractures to bending portions (fold, etc.) after bending (folding) the electrically conductive object (electrically conductive sheet).

The high tenacity/flexibility additives can contain at least one of the cross-linking agent and plasticizer. That is, (1) the high tenacity/flexibility additive contains the cross-linking agent but contains no plasticizer, or (2) the high tenacity/flexibility additive contains the plasticizer but contains no cross-linking agent.

In the case of (1), high tenacity, that is, both of tensile strength and tensile elongation (compared with Comparative Example (Comparative Example 1) where high tenacity/flexibility additive does not contain cross-linking agent or plasticizer) can be improved. Furthermore, flexibility can also be improved.

In the case of (2), although tensile strength is slightly decreased (tensile strength is within acceptable range), the tensile elongation can be significantly improved. Therefore, overall, high tenacity can be improved. Furthermore, flexibility can also be improved.

Preferably, high tenacity/flexibility additive contains both of the cross-linking agent and plasticizer. When both of the cross-linking agent and plasticizer are contained in the electrically conductive composition, even more excellently high tenacity can be given to the electrically conductive composition (furthermore, electrically conductive object to be described later).

The cross-linking agent can crosslink binder resin. This improves high tenacity of the electrically conductive composition to be given by the binder resin.

The cross-linking agent has reactivity with the hydroxyl group when the binder resin is a hydroxyl group-containing polymer. To be specific, examples of the cross-linking agent include a zirconium compound (for example, zirconium salt, etc.), titanium compound (for example, titanium salt, etc.), boric acid compound (for example, boric acid, etc.), alkoxy group-containing compound, methylol group-containing compound, isocyanate compound (for example, blocked isocyanate, etc.), and aldehyde compound (for example, dialdehyde such as glyoxal, etc.).

These can be used singly, or can be used in combination of two or more. In view of reactivity and stability, preferably, the zirconium compound, isocyanate compound, and aldehyde compound are used.

The ratio of the cross-linking agent relative to 100 parts by mass of the binder resin is, for example, 1 part by mass or more, preferably 10 parts by mass or more, and for example, 50 parts by mass or less, preferably 25 parts by mass or less. When the ratio is the above-described lower limit or more, and the above-described upper limit or less, excellently high tenacity and excellent flexibility can be given to the electrically conductive composition (furthermore, electrically conductive object to be described later).

The plasticizer plasticates the electrical conductive polymer. The plasticizer improves tensile elongation and flexibility of the electrically conductive composition. Examples of the plasticizer include polyol compounds such as glycerine, ethylene glycol, propylene glycol, sorbitol, and polymers thereof; and aprotic compounds such as N-methylpyrrolidone (NMP), dimethylformamide (DMF), N,N'-dimethylacetamide (DMAc), and dimethyl sulfoxide (DMSO). These can be used singly, or can be used in combination of two or more.

Preferably, in view of compatibility with other components, the polyol compound is used.

The ratio of the plasticizer relative to 100 parts by mass of the electrical conductive polymer is, for example, 100 parts by mass or more, preferably 300 parts by mass or more, and for example, 1000 parts by mass or less, preferably 600 parts by mass or less. When the ratio of the plasticizer is the above-described lower limit or more, excellent flexibility can be reliably given to the electrically conductive composition (furthermore, electrically conductive object to be described later). When the ratio of the plasticizer is the above-described upper limit or less, excellently high tenacity and excellent flexibility can be given to the electrically conductive composition (furthermore, electrically conductive object to be described later).

To the electrically conductive composition, for example, additives such as a surfactant can be added at a suitable ratio. Examples of the surfactant include silicone surfactants.

To prepare the electrically conductive composition, the above-described components are blended at the above-described ratio, and they are mixed. At that time, as necessary, a solvent is used at a suitable ratio. Examples of the solvent include organic solvents, and water-based solvents such as, for example, water. Preferably, the water-based solvent is used. The electrical conductive polymer and/or binder resin (preferably, water-soluble polymer) can be prepared as an aqueous solution, in which the electrical conductive polymer and/or binder resin are dissolved in the water-based solvent.

The electrically conductive composition is prepared (produced) as an electrically conductive composition liquid (aqueous solution of electrically conductive composition) in this manner.

Thereafter, an electrically conductive object such as an electrically conductive sheet is prepared from the electrically conductive composition.

To be specific, the electrically conductive composition liquid is applied on the surface of a substrate (release sheet, breadboard, etc.), and thereafter, dried to remove the solvent.

In this manner, the electrically conductive object is formed as an electrically conductive sheet.

Thereafter, the electrically conductive object is further treated with heat.

The heat treatment conditions are those conditions that allow the cross-linking agent to react. To be specific, the electrically conductive object is heated at a temperature of, for example, 100° C. or more, preferably 120° C. or more, and for example, 180° C. or less, preferably 160° C. or less, for, for example, 5 minutes or more, preferably 15 minutes or more, and for example, 300 minutes or less, preferably 120 minutes or less.

The heat treatment allows crosslinking reaction of the binder resin by the cross-linking agent to progress.

The electrically conductive object (electrically conductive sheet) is produced in this manner

[Physical Properties of Electrically Conductive Object]

The electrically conductive object is rubbery, and has both high tenacity and flexibility.

The electrically conductive object has a volume resistivity of, for example, $1 \times 10^{-2}$ Ω·m or less, preferably $5 \times 10^{-3}$ Ω·m or less. The volume resistivity measurement method is described in Examples later on.

High tenacity of the electrically conductive object (electrically conductive sheet) is evaluated by both of tensile strength and tensile elongation. The electrically conductive object (electrically conductive sheet) has a tensile strength of, for example, 2 $N/m^2$ or more, preferably 5 $N/m^2$ or more. The electrically conductive object (electrically conductive sheet) has a tensile elongation of, for example, 10% or more, preferably 50% or more.

Specifically, high tenacity is, for example, (1) tensile strength of 2 $N/m^2$ or more, and tensile elongation of 50% or more, and for example, (2) tensile strength of 5 $N/m^2$ or more, and tensile elongation of 10% or more. When the conditions of one of (1) and (2) is satisfied, the electrically conductive object (electrically conductive sheet) has high tenacity (has excellent high tenacity).

More preferably, high tenacity is (3) tensile strength is 5 $N/m^2$ or more, and tensile elongation of 50% or more.

The tensile strength and tensile elongation are described in Examples later on.

Flexibility is evaluated by, for example, two-fold test, and the fracture rate is, for example, less than 50%, preferably less than 20%.

Flexibility is described in Examples later on.

The electrically conductive composition contains at least one of the cross-linking agent and plasticizer, and therefore electrically conductive object with excellent high tenacity and flexibility can be prepared.

The electrically conductive object can be applied for use in which high tenacity and flexibility are required, for example, use for a living body, clothing, and wearable sensor.

[Biosensor]

Next, description is given below of a wearable biosensor 30 as an example of the biosensor including a connector as an example of the electrically conductive object with reference to FIG. 1 to FIG. 6C.

In FIG. 1, left-right direction on the sheet is longitudinal direction (first direction) of the wearable biosensor 30. Right side on the sheet is longitudinal one side (one side in first direction), left side on the sheet is longitudinal other side (the other side in first direction).

In FIG. 1, up-down direction on the sheet is transverse direction (direction orthogonal to longitudinal direction, width direction, second direction orthogonal to first direction) of the wearable biosensor 30. Upper side on the sheet is one side in transverse direction (one side in width direction, one side in second direction), and lower side on the sheet is the other side in transverse direction (the other side in width direction, the other side in second direction).

In FIG. 1, paper thickness direction on the sheet is up-down direction (thickness direction, third direction orthogonal to first direction and second direction) of the wearable biosensor 30. Near side on the sheet is upper side (one side in thickness direction, one side in third direction), and far side on the sheet is lower side (the other side in thickness direction, the other side in third direction).

The directions are in accordance with the direction arrows described in the figures.

These definitions of the directions are not intended to limit the orientations of the wearable biosensor 30 at the time of production and use.

Figure 2A:
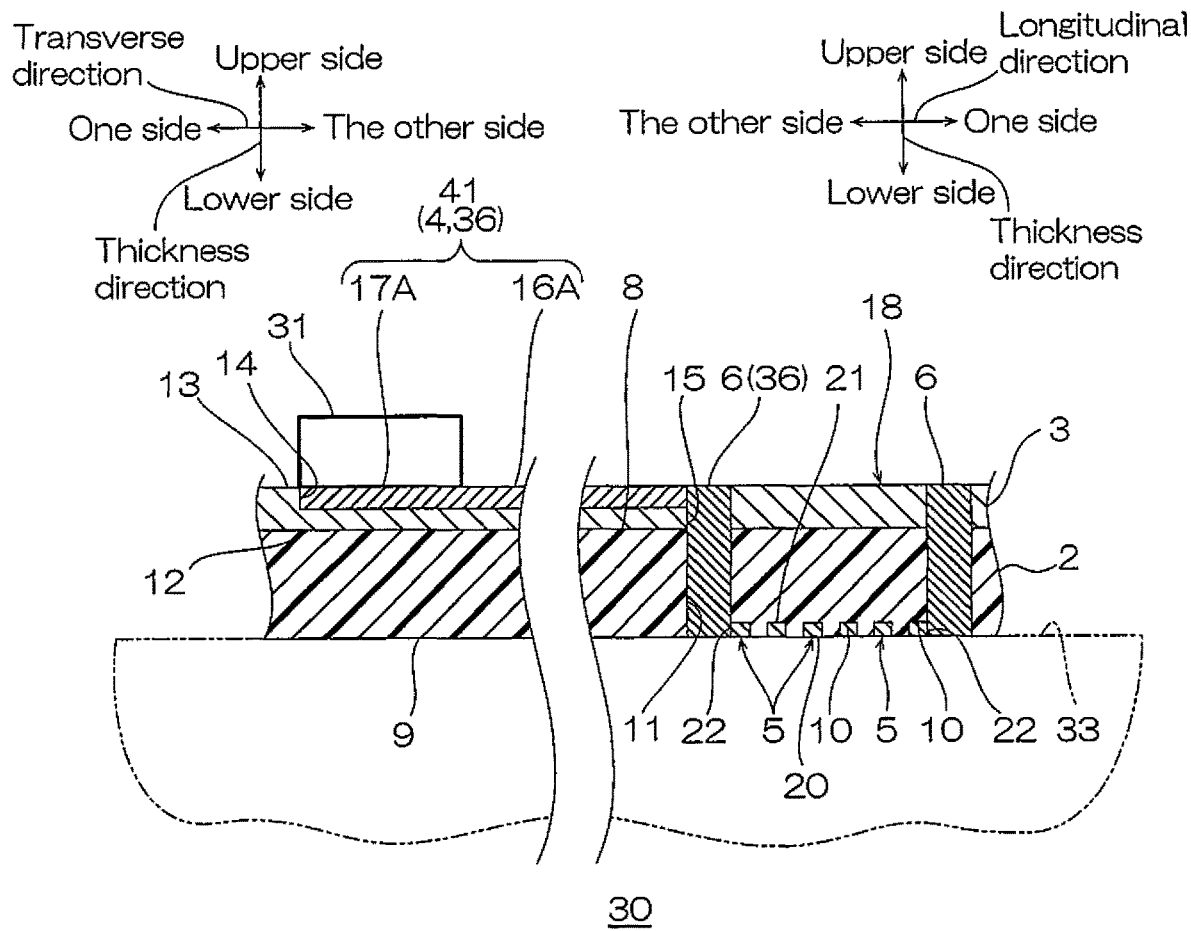
FIG. 2A and FIG. 2B are cross sectional views of the wearable biosensor shown in FIG. 1.
Figure 2B:
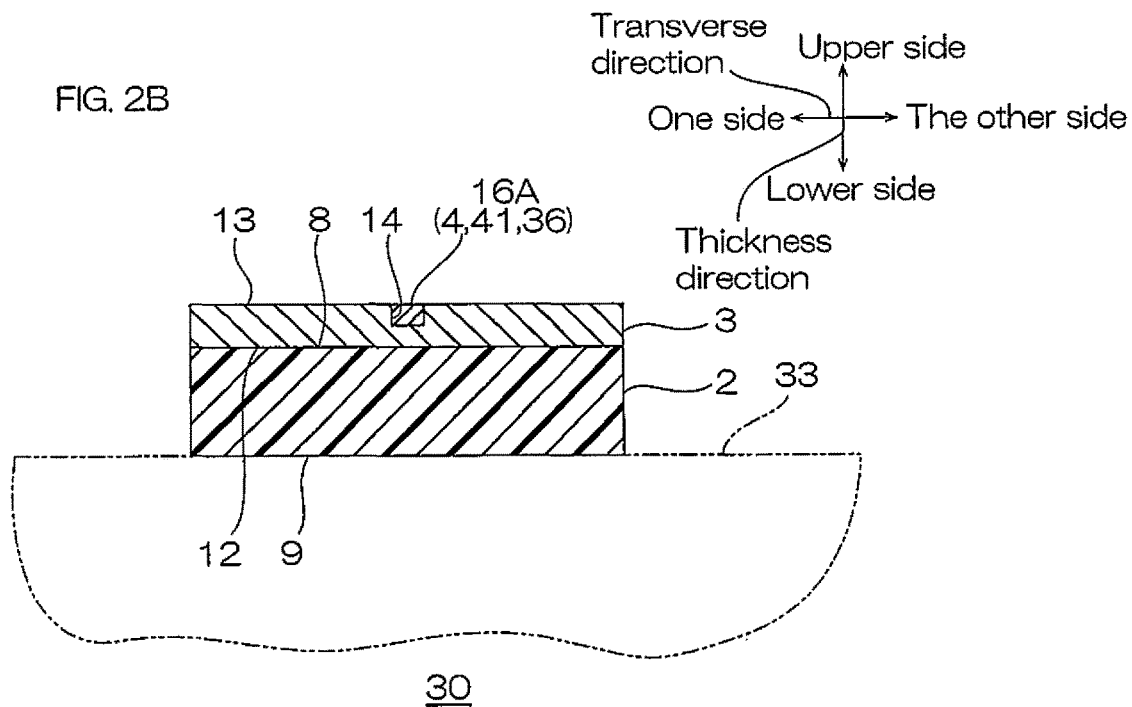

As shown in FIG. 1 to FIG. 2B, the wearable biosensor 30 has a substantially flat plate shape extending in longitudinal direction. The wearable biosensor 30 is a sheet having excellently high tenacity and flexibility. The wearable biosensor 30 includes a pressure-sensitive adhesive layer 2, a substrate layer 3 disposed on an adhesive upper face of the pressure-sensitive adhesive layer 2, a wire layer 4 disposed on the substrate layer 3, a probe 5 disposed on an adhesive lower face 9 of the pressure-sensitive adhesive layer 2, a connecter 6 as an example of the electrically conductive object that electrically connects the wire layer 4 with the probe 5, and an electronic component 31 electrically connected with the wire layer 4.

The pressure-sensitive adhesive layer 2 forms the lower face of the wearable biosensor 30. The pressure-sensitive adhesive layer 2 is a layer that gives pressure-sensitive adhesiveness to the lower face of the wearable biosensor 30 for attaching the lower face of the wearable biosensor 30 to the surface of the living body (skin 33 shown by phantom line, etc.). The pressure-sensitive adhesive layer 2 forms the outline shape of the wearable biosensor 30. The pressure-sensitive adhesive layer 2 has a flat plate shape extending in longitudinal direction. To be specific, the pressure-sensitive adhesive layer 2 has, for example, a band shape extending in longitudinal direction, with a longitudinal center portion bulging toward transverse both outsides. In the pressure-sensitive adhesive layer 2, both end edges in transverse direction of the longitudinal center portion are positioned at transverse both outsides relative to the both end edges in transverse direction of other than the longitudinal center portion.

The pressure-sensitive adhesive layer 2 has an adhesive upper face 8 and an adhesive lower face 9.

The adhesive upper face 8 has a flat face.

The adhesive lower face 9 is disposed to face each other at a lower side of the adhesive upper face 8 in spaced apart relation.

The pressure-sensitive adhesive layer 2 has two adhesion openings 11 at longitudinal both ends thereof. Each of the two adhesion openings 11 has a substantially ring shape in plan view. The adhesion opening 11 penetrates the pressure-sensitive adhesive layer 2 in thickness direction. The adhesion opening 11 is filled with the connecter 6.

The adhesive lower face 9 inside the adhesion opening 11 has adhesion grooves 10 in correspondence with the probe 5 (described later). The adhesion groove 10 is opened toward the lower side.

The material of the pressure-sensitive adhesive layer 2 is not particularly limited, as long as the material has pressure-sensitive adhesiveness.

The substrate layer 3 forms the upper face of the wearable biosensor 30 along with the electronic component 31 to be described later. The substrate layer 3 forms the outline shape of the wearable biosensor 30 along with the pressure-sensitive adhesive layer 2.

The shape in plan view of the substrate layer 3 is the same as the shape in plan view of the pressure-sensitive adhesive layer 2. The substrate layer 3 is disposed on the entire upper face of the pressure-sensitive adhesive layer 2 (but excluding the region where connecter 6 is provided). The substrate layer 3 is a support layer supporting the pressure-sensitive adhesive layer 2. The substrate layer 3 has a flat plate shape extending in longitudinal direction. The substrate layer 3 has a substrate lower face 12 and a substrate upper face 13.

The substrate lower face 12 has a flat face. The substrate lower face 12 is in contact with (pressure sensitive adhesion) the adhesive upper face 8 of the pressure-sensitive adhesive layer 2.

The substrate upper face 13 is disposed to face each other at the upper side of the substrate lower face 12 in spaced apart relation. The substrate upper face 13 has a substrate groove 14 in correspondence with the wire layer 4. The substrate groove 14 has the same pattern as that of the wire layer 4 in plan view. The substrate groove 14 is opened toward the upper side.

The substrate layer 3 has a substrate opening 15 in correspondence with the adhesion opening 11. The substrate opening 15 communicates with the adhesion opening 11 in thickness direction. The substrate opening 15 has a substantially ring shape in plan view with the same shape and the same size as those of the adhesion opening 11.

The material of the substrate layer 3 has, for example, a stretching property. The material of the substrate layer 3 has, for example, an insulating layer. For such a material, for example, resin such as polyurethane resin is used.

The substrate layer 3 has an elongation at break of, for example, 100% or more, preferably 200% or more, more preferably 300% or more, and for example, 2000% or less. When the elongation at break is the above-described lower limit or more, the material of the substrate layer 3 can have excellent stretching property.

The wire layer 4 is embedded in, for example, the substrate groove 14. To be specific, the wire layer 4 is embedded in the upper portion of the substrate layer 3 so as to be exposed from the substrate upper face 13 of the substrate layer 3. The wire layer 4 has an upper face and a lower face disposed in spaced apart relation from each other, and side faces connecting their peripheral end edges. The entire lower face and the entire side face are in contact with the substrate layer 3. The upper face is exposed from the substrate upper face 13 (excluding substrate groove 14). The upper face of the wire layer 4 forms the upper face of the wearable biosensor 30 along with the substrate upper face 13 and the electronic component 31.

The wire layer 4 has a wire pattern connecting the connecter 6, an electronic component 31 (described later), and a battery 32 (described later). To be specific, the wire layer 4 independently includes a first wire pattern 41 and a second wire pattern 42.

The first wire pattern 41 is disposed at longitudinal one side of the substrate layer 3. The first wire pattern 41 includes a first wire 16A, and a first terminal 17A and a second terminal 17B continuous therefrom.

The first wire pattern 41 has a substantially letter T-shape in plan view. To be specific, the first wire pattern 41 extends from the longitudinal one end portion (the connecter 6 positioned at) of the substrate layer 3 toward longitudinal other side, splits at the longitudinal center portion of the substrate layer 3, and extends toward transverse both outsides.

The first terminal 17A and the second terminal 17B each is disposed at transverse both end portions in longitudinal center portion of the substrate layer 3. The first terminal 17A and the second terminal 17B each has a substantially rectangular shape in plan view (land shape). The first terminal 17A and the second terminal 17B each is continuous with both end portions of the first wire 16A extending in transverse both outsides at a longitudinal center portion of the substrate layer 3.

The second wire pattern 42 is provided in spaced apart relation at longitudinal other side of the first wire pattern 41. The second wire pattern 42 includes a second wire 16B and a third terminal 17C and a fourth terminal 17D continuous therefrom.

The second wire pattern 42 has a substantially letter T-shape in plan view. To be specific, the second wire pattern 42 extends from (the connecter 6 positioned at) the longitudinal other end portion of the substrate layer 3 toward longitudinal one side, splits at the longitudinal center portion of the substrate layer 3, and extends toward transverse both outsides.

The third terminal 17C and the fourth terminal 17D each is disposed at transverse both end portions in longitudinal center portion of the substrate layer 3. The third terminal 17C and the fourth terminal 17D each has a substantially rectangular shape in plan view (land shape). The third terminal 17C and the fourth terminal 17D each is continuous with both end portions of the second wire 16B extending in transverse both outsides at a longitudinal center portion of the substrate layer 3.

For the material of the wire layer 4, for example, conductors such as copper, nickel, gold, and alloys thereof are used. For the material of the wire layer 4, preferably, copper is used.

The probe 5 is an electrode that allows sensing of electric signals, temperatures, vibrations, sweat, and metabolite from a living body, when the pressure-sensitive adhesive layer 2 is attached to the skin 33 by making contact with the skin 33. The probe 5 is embedded in the pressure-sensitive adhesive layer 2 so as to be exposed from the adhesive lower face 9 of the pressure-sensitive adhesive layer 2. That is, the probe 5 is embedded in the adhesion groove 10 of the pressure-sensitive adhesive layer 2 at the inside of the adhesion opening 11. The probe 5 is disposed at the adhesive lower face 9 forming the adhesion groove 10. That is, the probe 5 is embedded in the lower end portion of the pressure-sensitive adhesive layer 2 at the inside of the adhesion opening 11. The probe 5 has a mesh shape, preferably, a substantially grid shape in plan view (or has a substantially mesh shape). In other words, the probe 5 has holes in spaced apart relation in the surface direction (longitudinal direction and transverse direction). The hole is filled with the pressure-sensitive adhesive layer 2.

The probe 5 has a substantially rectangular shape in cross sectional view extending in a direction orthogonal thereto. The probe 5 has a probe lower face 20, a probe upper face 21 disposed to face the upper side of the probe lower face 20 in spaced apart relation, and side faces connecting peripheral end edges of the probe lower face 20 and the probe upper face 21.

The probe lower face 20 is exposed from the adhesive lower face 9 (excluding adhesion groove 10) of the pressure-sensitive adhesive layer 2. The probe lower face 20 is flush with the adhesive lower face 9. The probe lower face 20 forms the lower face of the wearable biosensor 30 along with the adhesive lower face 9.

The probe upper face 21 and the side face are covered with the pressure-sensitive adhesive layer 2.

As shown in FIG. 5, of the side faces of the probe 5, the face positioned at the outermost side is an outer side face 22. The outer side face 22 forms a virtual circle passing through the outer side face 22 in plan view.

For the material of the probe 5, those materials given as Examples of the wire layer 4 (to be specific, conductor) are used.

The external size of the probe 5 is set so that the virtual circle passing through the outer side face 22 overlaps with the inner periphery defining the adhesion opening 11 in plan view.

The connector 6 is prepared from the above-described electrically conductive composition, and is an example of the electrically conductive object to be formed. The connecter 6 is provided in correspondence with the substrate opening 15 and the adhesion opening 11, and has the same shape as these. The connecter 6 penetrates (pass through) the substrate layer 3 and the pressure-sensitive adhesive layer 2 in thickness direction (up-down direction), and the substrate opening 15 and the adhesion opening 11 are filled with the connecter 6. The connecter 6 has a no-end shape in plan view along the outer side face 22 of the probe 5. To be specific, the connecter 6 has a substantially cylindrical shape with its axis line extending in thickness direction (along virtual circle passing through the outer side face 22).

The inner side face of the connecter 6 is in contact with the outer side face 22 of the probe 5.

The connecter 6 is allowed to adhere to the pressure-sensitive adhesive layer 2 outside the adhesion opening 11 and the pressure-sensitive adhesive layer 2 inside the adhesion opening 11 by pressure-sensitive adhesion. The connecter 6 is in contact with the substrate layer 3 outside the substrate opening 15 and the substrate layer 3 inside the substrate opening 15.

The upper face of the connecter 6 is flush with the substrate upper face 13. The lower face of the connecter 6 is flush with the adhesive lower face 9.

As shown in FIG. 1, of the two connecters 6, the connecter 6 positioned at longitudinal one side is continuous with, at its upper end portion, longitudinal one end edge of the wire 16A positioned at longitudinal one side.

The connecter 6 positioned at longitudinal other side is continuous with, at its upper end portion, longitudinal other end edge of the wire 16B positioned at longitudinal other side.

That is, the connecter 6 is electrically connected with the wire layer 4.

In this manner, the connecter 6 electrically connects the wire layer 4 with the probe 5.

The connecter 6 and the wire layer 4 form a circuit portion 36 that electrically connects the probe 5 with the electronic component 31. That is, the circuit portion 36 includes the wire layer 4 disposed on the substrate upper face 13 of the substrate layer 3, and the connecter 6 passing through the substrate layer 3 and the pressure-sensitive adhesive layer 2. Preferably, the circuit portion 36 is composed only of the wire layer 4 and the connecter 6.

The connector 6 has a radial direction length (half the value of deduction of internal diameter from external diameter) of, for example, 1 µm or more, preferably 100 µm or more, and for example, less than 2000 µm, preferably 1000 µm or less, more preferably 500 µm or less.

Examples of the electronic component 31 include an analog front-end, microcomputer, and memory for processing and storing electric signals from a living body obtained by the probe 5, and a communication IC and transmitter for converting electric signals to electro-magnetic waves and wirelessly transmitting them to an external receiver.

To be more specific, when the wearable biosensor 30 is a wearable electrocardiograph, the changes in cardiac potential obtained at the probe 5 is converted to digital data at an analog front-end, and the changes in the cardiac potential is stored in the memory. For example, changes in the cardiac potential are stored in the memory with 16 bit, at a data rate of 1 kHz. To decrease the memory size, sometimes resolving power of data and data rate have to be decreased. After detaching the wearable biosensor 30 after the measurement, the stored data is taken out from the memory and analyzed. The communication IC has functions to send the signals obtained at the probe 5 to outside wirelessly. This function works when connected under normal communication, the wearable biosensor 30 is attached to the skin 33, and when it can be confirmed that data acquisition is normal, and a message that the data acquisition is normal is intermittently sent to outside, to check if the wearable biosensor 30 is working normally.

The electronic component 31 can have some or all of the above-described components. The electronic component 31 is in contact with the substrate upper face 13. The electronic component 31 has a substantially rectangular flat plate shape in cross sectional view. Two terminals 35 are provided at the lower face of the electronic component 31. Two terminals 35 of the electronic component 31 are electrically connected with the first terminal 17A and the third terminal 17C, respectively. The electronic component 31 is harder than, for example, the pressure-sensitive adhesive layer 2 and the substrate layer 3.

Next, description is given below of the method for producing a wearable biosensor 30.

As shown in FIG. 3A, in this method, first, the substrate layer 3 and wire layer 4 are prepared.

For example, the substrate layer 3 and wire layer 4 are prepared so that the wire layer 4 is embedded in the substrate groove 14 by the method described in Japanese Unexamined Patent Publication No. 2017-22236 and Japanese Unexamined Patent Publication No. 2017-22237.

As shown in FIG. 3B, then, the pressure-sensitive adhesive layer 2 is disposed on the substrate lower face 12.

To dispose the pressure-sensitive adhesive layer 2 on the substrate lower face 12, for example, first, an application liquid containing the materials for the pressure-sensitive adhesive layer 2 is prepared, and then the application liquid is applied on the upper face of the first release sheet 19, and thereafter, they are dried by heating. In this manner, the pressure-sensitive adhesive layer 2 is disposed on the upper face of the first release sheet 19. The first release sheet 19 has, for example, a substantially flat plate shape extending in longitudinal direction. For the material of the first release sheet 19, for example, resin such as polyethylene terephthalate is used.

Then, the pressure-sensitive adhesive layer 2 and the substrate layer 3 are bonded by, for example, a laminator. To be specific, the adhesive upper face 8 of the pressure-sensitive adhesive layer 2 is brought into contact with the substrate lower face 12 of the substrate layer 3.

At this point, the substrate layer 3 or the pressure-sensitive adhesive layer 2 has no substrate opening 15 or adhesion opening 11.

As shown in FIG. 3C, then, the opening 23 is formed in the substrate layer 3 and the pressure-sensitive adhesive layer 2.

The opening 23 penetrates the substrate layer 3 and pressure-sensitive adhesive layer 2. The opening 23 is a hole having a generally circular shape in plan view (through opening) defined by an outer peripheral face defining the substrate opening 15 and an outer peripheral face defining the adhesion opening 11. The opening 23 is opened toward the upper side. Meanwhile, the lower end of the opening 23 is closed by the first release sheet 19.

To form the opening 23, the pressure-sensitive adhesive layer 2 and substrate layer 3 are subjected to, for example, punching or half etching.

Then, the probe member 18 is prepared, and inserted into the opening 23.

Figure 4:
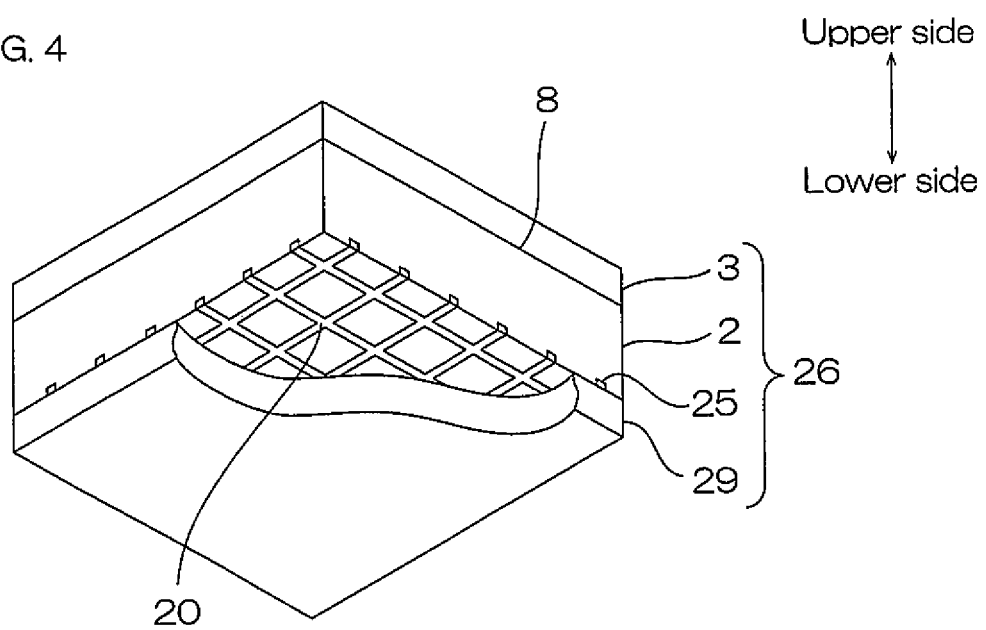
FIG. 4 shows a perspective view of the probe-containing sheet seen from the bottom, with a partially cut out second release sheet.
Figure 6A:
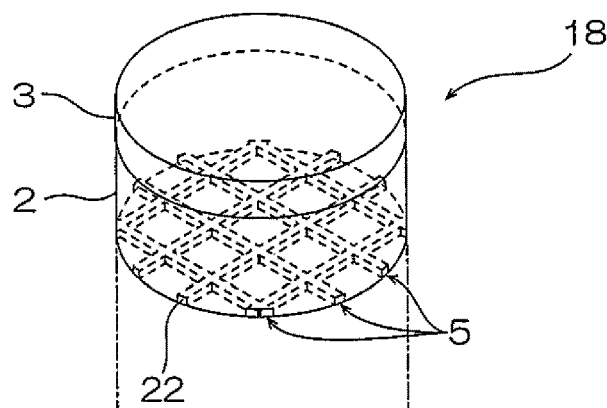
FIG. 6A to FIG. 6C are exploded perspective views of the probe member, FIG. 6A showing the probe member, FIG. 6B showing a connector, and FIG. 6C showing an opening at a longitudinal one end of the wearable biosensor.
Figure 6B:
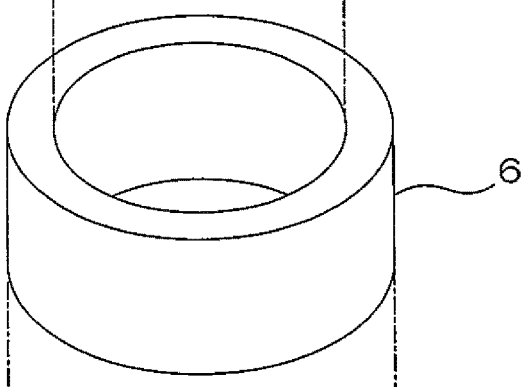
Figure 6C:
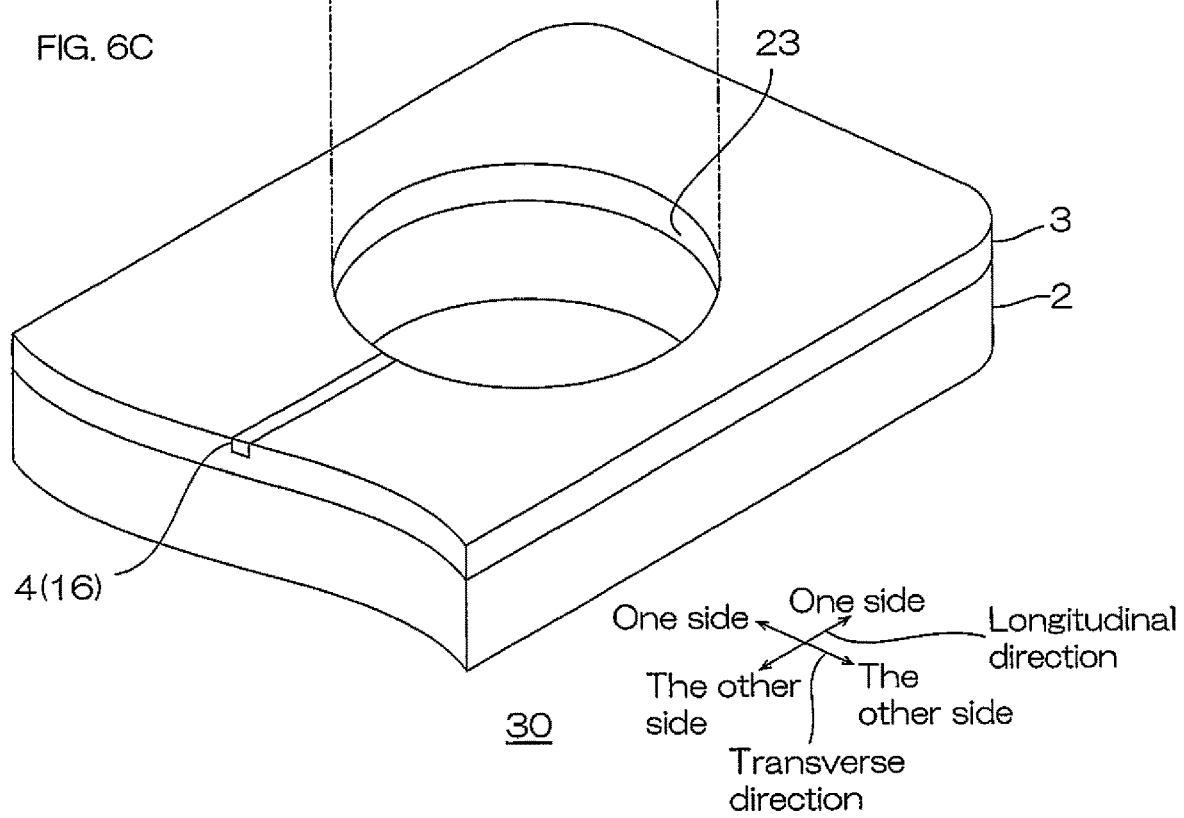

As shown in FIG. 4, to prepare the probe member 18, first, the probe-containing sheet 26 is prepared.

The probe-containing sheet 26 includes a second release sheet 29, a probe pattern 25 formed on the second release sheet 29, a pressure-sensitive adhesive layer 2 formed on the second release sheet 29 and in which the probe pattern 25 is embedded, and a substrate layer 3 disposed on the adhesive upper face 8 of the pressure-sensitive adhesive layer 2.

The second release sheet 29 has the same configuration as that of the above-described first release sheet 19.

The probe pattern 25 has the same pattern as that of the probe 5, and the material of the probe pattern 25 is the same as the material of the probe 5. The probe pattern 25 has a flat area larger than the virtual circle passing through the outer side face 22 of the probe 5.

The pressure-sensitive adhesive layer 2 and substrate layer 3 of the probe-containing sheet 26 has the same configuration as that of the above-described pressure-sensitive adhesive layer 2 and substrate layer 3.

The probe-containing sheet 26 is prepared, for example, by the method described in Japanese Unexamined Patent Publication No. 2017-22236 and Japanese Unexamined Patent Publication No. 2017-22237.

Although not shown, to be specific, after forming a seed layer composed of copper on the upper face of a release layer composed of stainless steel, a photoresist is laminated on the entire upper face of the seed layer. Then, the photoresist is exposed to light and developed, thereby forming the photoresist into a reverse pattern of the probe pattern 25. Then, after the probe pattern 25 is formed on the upper face of the seed layer by electrolytic plating, the photoresist is removed. Thereafter, an application liquid containing the material of the pressure-sensitive adhesive layer 2 is applied to cover the probe pattern 25, and cured to form the pressure-sensitive adhesive layer 2. Then, the substrate layer 3 is bonded to the upper face of the pressure-sensitive adhesive layer 2 by, for example, a laminator. Then, the release layer is removed from the lower face of the seed layer, and then the seed layer is removed. Thereafter, as necessary, the second release sheet 29 is bonded to the lower face of the pressure-sensitive adhesive layer 2.

In this manner, the probe-containing sheet 26 is prepared.

As shown in FIG. 5, then, a cutting line 27 is formed on the probe pattern 25, pressure-sensitive adhesive layer 2, and substrate layer 3 into a generally circular shape in plan view. The cutting line 27 is formed, for example, by punching. The cutting line 27 divides the probe pattern 25, pressure-sensitive adhesive layer 2, and substrate layer 3 into inner portions and outer portions, but the cutting line 27 is not formed on the second release sheet 29. The size of the cutting line 27 is the same as the internal diameter of the adhesion opening 11 and substrate opening 15. That is, the cutting line 27 coincides with the virtual circle passing through the outer side face 22.

By forming the cutting line 27, the probe member 18 is formed.

In the probe member 18, the outer side face 22 of the probe 5 is flush with the outer side face of the pressure-sensitive adhesive layer 2. In the probe member 18, the outer side face 22 is exposed to the outside in radial direction from the outer side face of the pressure-sensitive adhesive layer 2.

Then, as shown in the arrow in FIG. 5, the probe member 18 is pulled out from the second release sheet 29. To be specific, the adhesive lower face 9 and probe lower face 20 of the probe member 18 are released from the second release sheet 29.

Thereafter, as shown by the arrow in FIG. 3C, the probe member 18 is inserted in the opening 23.

At this time, a gap is created between the pressure-sensitive adhesive layer 2, substrate layer 3, and probe 5 of the probe member 18, and the pressure-sensitive adhesive layer 2 and substrate layer 3 surrounding the opening 23. That is, the probe member 18 is inserted into the opening 23 so as to form the substrate opening 15 and the adhesion opening 11.

Thereafter, as shown in FIG. 3D, the connecter 6 is provided in the substrate opening 15 and the adhesion opening 11.

To be specific, the electrically conductive resin composition (electrically conductive composition liquid) is injected (or applied) to the substrate opening 15 and adhesive opening 11. Thereafter, the electrically conductive resin composition (electrically conductive composition liquid) is heated to remove the solvent, and to crosslink the binder resin with the cross-linking agent.

In this manner, the biosensor laminate 1 including the first release sheet 19, pressure-sensitive adhesive layer 2, substrate layer 3, wire layer 4, probe 5, and connecter 6 is produced. The biosensor laminate 1 is distributed singly, and is an industrially applicable device. To be specific, the biosensor laminate 1 can be distributed singly, separately from the electronic component 31 and battery 32 (ref: phantom line in FIG. 1) to be described later. That is, the biosensor laminate 1 is not mounted with the electronic component 31 or battery 32, and is a component for producing a wearable biosensor 30.

As shown in FIG. 1, thereafter, the two terminals 35 of the electronic components 31 are electrically connected with the first terminal 17A and the third terminal 17C. At this time, the lower face of the electronic component 31 is allowed to contact the substrate upper face 13.

In this manner, the wearable biosensor 30 is produced.

The wearable biosensor 30 includes a pressure-sensitive adhesive layer 2, a substrate layer 3, a wire layer 4, a probe 5, a connecter 6, an electronic component 31, and a first release sheet 19, and preferably, is composed only of these. As shown in FIG. 2A, the wearable biosensor 30 may be composed only of the pressure-sensitive adhesive layer 2, substrate layer 3, wire layer 4, probe 5, connecter 6, and electronic component 31 without including the first release sheet 19.

Next, description is given below of a method of using the wearable biosensor 30.

To use the wearable biosensor 30, first, the battery 32 is mounted on the wearable biosensor 30.

The battery 32 has a substantially flat plate (box) shape extending in surface direction. The battery 32 has two terminals (not shown) provided at its lower face.

To allow the battery 32 to be mounted on the wearable biosensor 30, the two terminals (not shown) of the battery 32 are electrically connected with the second terminal 17B and fourth terminal 17D.

At that time, the lower face of the battery 32 is allowed to contact the substrate upper face 13.

Then, the first release sheet 19 (ref: arrow and phantom line of FIG. 3D) is released from the pressure-sensitive adhesive layer 2 and probe 5.

As shown in the phantom line in FIG. 2A, then, the adhesive lower face 9 of the pressure-sensitive adhesive layer 2 is allowed to contact, for example, a skin 33 of a human body. To be specific, the pressure-sensitive adhesive layer 2 is allowed to pressure-sensitively adhere to a surface of the skin 33.

Then, the probe lower face 20 of the probe 5 makes contact with the surface of the skin 33, by allowing the adhesive lower face 9 to pressure-sensitively adhere (attaching) to the skin 33.

Then, the probe 5 senses electric signals from the living body, and the electric signals sensed at the probe 5 are inputted to the electronic component 31 through the connecter 6 and wire layer 4. The electronic component 31 processes the electric signal based on the electric power supplied from the battery 32, and store that information. Furthermore, as necessary, the electric signals are converted to electro-magnetic waves, and they are wirelessly transmitted to an external receiver.

Examples of the wearable biosensor 30 include devices that can sense electric signals of a living body and monitor conditions of a living body, and to be specific, a wearable electrocardiograph, wearable electroencephalograph, wearable sphygmomanometer, wearable pulse meter, wearable electromyograph, wearable thermometer, and wearable accelerometer. These devices can be individual devices, or can be a device including the plurality of these devices.

The wearable biosensor 30 is preferably used as a wearable electrocardiograph. In the wearable electrocardiograph, the probe 5 senses cardiac action potential as electric signals.

The living body includes a human body and a living thing other than the human body, but preferably, the living body is a human body.

In the wearable biosensor 30, the connector 6 is prepared from the above-described electrically conductive composition, and therefore it flexibly conforms to the contraction of the skin 33, and also has excellent durability. Therefore, in the wearable biosensor 30, connection reliability with the connector 6 is excellent, and sensing reliability is excellent.

In the above-described description, the connector 6 is cylindrical, but the shape is not particularly limited, and for example, it can have a prism shape.

EXAMPLES

The specific numerical values of mixing ratio (content), physical property value, and parameter used in the description below can be replaced with the upper limit values (numerical values defined with "or less" or "below") or lower limit values (numerical values defined with "or more" or "more than") of the corresponding numerical values of mixing ratio (content), physical property value, and parameter described in "DESCRIPTION OF EMBODIMENTS" above.

The components used in Examples are shown below.
PH1000: trade name [Clevious PH1000], PEDOT-PSS (electrical conductive polymer) aqueous solution, manufactured by Heraeus Holding
Gohsenx Z-410: modified polyvinyl alcohol (acetoacetyl group-containing polyvinyl alcohol) 10% aqueous solution, manufactured by The Nippon Synthetic Chemical Industry Co., Ltd.
KURANOL: modified polyvinyl alcohol (acetoacetyl group-containing poly vinyl alcohol) 10% aqueous solution
Safelink SPM-01: 10% aqueous solution of cross-linking agent (zirconium compound), manufactured by The Nippon Synthetic Chemical Industry Co., Ltd.
SU-268A: manufactured by Meisei Chemical Works, Ltd.
Polyethylene glycol 600: polyethylene glycol with number average molecular weight of 570 to 630
SILFACE SAG503A: silicone-based surfactant, manufactured by Nissin Chemical co., ltd.

Example 1

19.0 g of PEDOT-PSS (electrical conductive polymer) aqueous solution (Clevious PH1000, manufactured by Heraeus Holding), 5.0 g of 10% aqueous solution of modified polyvinyl alcohol) (Gohsenx Z-410, manufactured by The Nippon Synthetic Chemical Industry Co., Ltd.), 1.0 g of 10% aqueous solution (Safelink SPM-01, manufactured by The Nippon Synthetic Chemical Industry Co., Ltd.) of cross-linking agent (zirconium compound), 1.0 g of plasticizer (glycerine, manufactured by Wako Pure Chemical Industries, Ltd.), and 0.04 g of surfactant (SILFACE SAG503A, manufactured by Nissin Chemical co., ltd.) were blended, and mixed for 30 minutes in an ultrasonic bath, thereby preparing a homogenous electrically conductive composition aqueous solution.

Then, the electrically conductive composition aqueous solution was applied on a PET (polyethylene terephthalate) film using an applicator, and thereafter, dried in a drying oven at 90° C. for 30 minutes, and then heated at 120° C. for 15 minutes to be subjected to cross-linking, thereby forming an electrically conductive sheet (prepared).

The electrically conductive sheet was blue black and rubbery.

Example 2 to Comparative Example 1

An electrically conductive sheet was formed (prepared) in the same manner as in Example 1, except that the formulation of the components was changed in accordance with Table 1.

(Evaluation)
(Volume Resistivity)
The volume resistivity of the electrically conductive sheet was measured and calculated with 4 terminal sensing method using a digital multimeter (manufactured by ADVANTEST R6552).

(High Tenacity)
The electrically conductive sheet was subjected to tensile test with the following conditions, and tensile strength and tensile elongation were calculated by the fracture point stress value.
Device: TENSILON Universal Testing Machine (manufactured by A&D Company, Limited RTF)
Size: 5 mm width, thickness 20 μm
Distance between chucks: 10 mm
Tensile speed: 10 mm/min
Measurement environment: 20° C., humidity 60% RH Then, tensile strength and tensile elongation were evaluated based on the criteria below, and then overall high tenacity was evaluated based on the results.

<Tensile Strength>
Excellent: 5 N/m$^2$ or more
Good: 2 N/m$^2$ or more, less than 5 N/m$^2$
Bad: less than 2 N/m$^2$ <Tensile Elongation>
Excellent: 50% or more
Good: 10% or more and less than 50%
Bad: less than 10%

<Evaluation on High Tenacity>
Excellent: Both of tensile strength and tensile elongation are Excellent
Good: One of tensile strength and tensile elongation is Excellent and the other is Good
Bad: None of the above (at least one of tensile strength and tensile elongation is Bad, or both are Good)

(Flexibility)
The electrically conductive sheet having a width of 10 mm, length of 30 mm, and thickness of 20 μm was folded into two so that the fold was along the width direction. Ten electrically conductive sheets were folded in this manner Then, the fracture rate (for example, fracture rate is 20% when two electrically conductive sheets out of the ten fractured) of the fold of the electrically conductive sheet folded into two was determined, and flexibility was evaluated based on the following.
Excellent: fracture rate was less than 20%
Good: fracture rate was 20% or more and less than 50%
Bad: fracture rate was 50% or more

TABLE 1

| Components | Type | Trade name | | Ex. 1 | Ex. 2 | Ex. 3 | Ex. 4 | Ex. 5 | Ex. 6 |
|---|---|---|---|---|---|---|---|---|---|
| Electrically conductive polymer | PEDOT-PSS | PH1000 (1% solution) | Commercially available product | 19.0 | 19.0 | 19.0 | 19.0 | 19.0 | 19.0 |
| Binder resin | PVA | Gohsenx Z-410 (10% aqueous solution) | 10% aqueous solution | 5.0 | — | 2.5 | 5.0 | 5.0 | 5.0 |
| | | KURANOL | 10% aqueous solution | — | 5.0 | 2.5 | — | — | — |
| Cross-linking agent | Zirconium | Safelink SPM-01 | 10% aqueous solution | 1.0 | 1.0 | 1.0 | — | — | 1.0 |
| | Dialdehyde | Glyoxal | 10% aqueous solution | — | — | — | 1.0 | — | — |
| | Blocked isocyanate | SU-268A | | — | — | — | — | 0.5 | — |
| Plasticizer | | Glycerine | | 1.0 | 1.0 | 1.0 | 1.0 | 1.0 | — |
| | | Propylene glycol | | — | — | — | — | — | 1.0 |
| | | Poly ethylene glycol#600 | | — | — | — | — | — | — |
| Surfactant | | SILFACE SAG503A | | 0.04 | 0.04 | 0.04 | 0.04 | 0.04 | 0.04 |
| Evaluation | | Total | | 26.0 | 26.0 | 26.0 | 26.0 | 25.5 | 26.0 |
| | | Resistance value (Actual measured value) | Ω | 20 | 70 | 50 | 40 | 41 | 26 |
| | Electrical conductivity | Volume resistivity | Ω·m | 4.0 × 10$^{-4}$ | 1.4 × 10$^{-3}$ | 1.0 × 10$^{-3}$ | 8.0 × 10$^{-4}$ | 8.2 × 10$^{-4}$ | 5.2 × 10$^{-4}$ |
| | | Results | | Excellent | Excellent | Excellent | Excellent | Excellent | Excellent |
| | High tenacity | Tensile strength | N/m$^2$ | 11.0 | 8.5 | 8.8 | 10.4 | 9.7 | 10.2 |
| | | Results | | Excellent | Excellent | Excellent | Excellent | Excellent | Excellent |
| | | Tensile elongation | % | 186 | 168 | 174 | 170 | 160 | 178 |
| | | Results | | Excellent | Excellent | Excellent | Excellent | Excellent | Excellent |
| | | High tenacity results | | Excellent | Excellent | Excellent | Excellent | Excellent | Excellent |
| | Flexibility | Two-fold durability | Fracture rate | 0% | 0% | 0% | 0% | 0% | 0% |

TABLE 1-continued

| Components | Type | Trade name | | Ex. 7 | Ex. 8 | Ex. 9 | Ex. 10 | Comp. Ex. 1 |
|---|---|---|---|---|---|---|---|---|
| Electrically conductive polymer | PEDOT-PSS | PH1000 (1% solution) | Commercially available product | 19.0 | 19.0 | 19.0 | 19.0 | 19.0 |
| Binder resin | PVA | Gohsenx Z-410 (10% aqueous solution) | 10% aqueous solution | 5.0 | 5.0 | 5.0 | 5.0 | 5.0 |
| | | KURANOL | 10% aqueous solution | — | — | — | — | — |
| Cross-linking agent | Zirconium | Safelink SPM-01 | 10% aqueous solution | 1.0 | 1.0 | 1.0 | — | — |
| | Dialdehyde | Glyoxal | 10% aqueous solution | — | — | — | — | — |
| | Blocked isocyanate | SU-268A | | — | — | — | — | — |
| Plasticizer | | Glycerine | | — | 1.3 | — | 1.0 | — |
| | | Propylene glycol | | — | — | — | — | — |
| | | Poly ethylene glycol#600 | | 1.0 | — | — | — | — |
| Surfactant | | SILFACE SAG503A | | 0.04 | 0.04 | 0.04 | 0.04 | 0.04 |
| Evaluation | | Total | | 26.0 | 26.3 | 25.0 | 25.0 | 24.0 |
| | | Resistance value (Actual measured value) | $\Omega$ | 26 | 18 | 350 | 3 | 10 |
| | Electrical conductivity | Volume resistivity | $\Omega \cdot m$ | $5.2 \times 10^{-4}$ | $3.6 \times 10^{-4}$ | $7.0 \times 10^{-3}$ | $6.0 \times 10^{-5}$ | $2.0 \times 10^{-4}$ |
| | | | Results | Excellent | Excellent | Excellent | Excellent | Excellent |
| | High tenacity | Tensile strength | $N/m^2$ | 11.5 | 7.4 | 32.6 | 4.5 | 28.0 |
| | | | Results | Excellent | Excellent | Excellent | Good | Excellent |
| | | Tensile elongation | % | 182 | 155 | 23 | 140 | 9 |
| | | | Results | Excellent | Excellent | Good | Excellent | Bad |
| | | High tenacity results | | Excellent | Excellent | Good | Good | Bad |
| | Flexibility | Two-fold durability | Fracture rate | 0% | 0% | 20% | 0% | 10% |

While the illustrative embodiments of the present invention are provided in the above description, such is for illustrative purpose only and it is not to be construed as limiting in any manner Modification and variation of the present invention that will be obvious to those skilled in the art is to be covered by the following claims.

INDUSTRIAL APPLICABILITY

The electrically conductive composition is used for a connector of a biosensor.

DESCRIPTION OF REFERENCE NUMERALS 4 wire layer
5 probe
6 connector
30 wearable biosensor
33 skin

The invention claimed is:

1. An electrically conductive composition comprising:
an electrical conductive polymer,
a binder resin, and
a plasticizer,
wherein
the plasticizer contains a polyol compound, and
the polyol compound is glycerine, and
a ratio of the glycerine relative to 100 parts by mass of the electrical conductive polymer is 300 parts by mass or more and 1,000 parts by mass or less.

2. The electrically conductive composition according to claim 1, further comprising a cross-linking agent.

3. The electrically conductive composition according to claim 1, wherein
the binder resin is a water-soluble polymer.

4. The electrically conductive composition according to claim 2, wherein
the cross-linking agent contains at least one selected from the group consisting of a zirconium compound, an isocyanate compound, and an aldehyde compound.

5. A biosensor comprising:
a wire layer,
a probe that makes contact with a surface of a living body, and
a connector that electrically connects the wire layer with the probe,
wherein the connector is prepared from the electrically conductive composition according to claim 1.

* * * * *